(12) United States Patent  
Silvestrini

(10) Patent No.: US 8,545,430 B2
(45) Date of Patent: *Oct. 1, 2013

(54) EXPANDABLE OCULAR DEVICES

(75) Inventor: Thomas A. Silvestrini, Alamo, CA (US)

(73) Assignee: Transcend Medical, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/157,180

(22) Filed: Jun. 9, 2011

(65) Prior Publication Data

US 2012/0035524 A1     Feb. 9, 2012

Related U.S. Application Data

(60) Provisional application No. 61/353,162, filed on Jun. 9, 2010.

(51) Int. Cl.
    *A61B 19/00*         (2006.01)

(52) U.S. Cl.
    USPC .............................................. 604/8; 623/1.12

(58) Field of Classification Search
    None
    See application file for complete search history.

(56) References Cited

U.S. PATENT DOCUMENTS

| | | | |
|---|---|---|---|
| 3,159,161 A | 12/1964 | Ness | |
| 4,370,760 A | 2/1983 | Kelman | |
| 4,457,757 A | 7/1984 | Molteno | |
| 4,558,698 A | 12/1985 | O'Dell | |
| 4,907,586 A | 3/1990 | Bille et al. | |
| 4,936,825 A | 6/1990 | Ungerleider | |
| 5,171,252 A | 12/1992 | Friedland | |
| 5,180,362 A | 1/1993 | Worst | |
| 5,356,064 A | 10/1994 | Green et al. | |
| 5,360,399 A | 11/1994 | Stegmann | |
| 5,370,607 A | 12/1994 | Memmen | |
| 5,370,641 A | 12/1994 | O'Donnell, Jr. | |
| 5,417,209 A | 5/1995 | Morrision | |
| 5,486,165 A | 1/1996 | Stegmann | |
| 5,536,274 A | 7/1996 | Neuss | |
| 5,601,548 A | 2/1997 | Smith et al. | |
| 5,626,558 A | 5/1997 | Suson | |

(Continued)

FOREIGN PATENT DOCUMENTS

WO      WO 95/08310      3/1995
WO      WO 2004/002337      1/2004

(Continued)

*Primary Examiner* — Leslie Deak
*Assistant Examiner* — Sara Sass
(74) *Attorney, Agent, or Firm* — Fred C. Hernandez; Mintz Levin Cohn Ferris Glovsky and Popeo, P.C.

(57) ABSTRACT

Disclosed herein are systems, devices and methods for treating an ocular disorder in an eye. The ocular device includes a proximal end, a distal end, and an internal lumen forming a flow pathway extending from the proximal end to the distal end; at least one inflow region that communicates with the flow pathway; and an expandable portion having a plurality of interconnected struts forming multiple openings in the device communicating with the flow pathway. The expandable portion has a first cross-sectional shape suitable for insertion into the eye that is generally cylindrical and a second cross-sectional shape that is larger than the first cross-sectional shape. The system also includes a delivery device for inserting the ocular device into an eye including a sheath configured to surround at least a portion of the ocular device; an applier configured to insert into the internal lumen of the ocular device; and an actuator.

26 Claims, 15 Drawing Sheets

(56) References Cited

U.S. PATENT DOCUMENTS

| | | |
|---|---|---|
| 5,626,559 A | 5/1997 | Solomon |
| 5,630,827 A | 5/1997 | Vijfvinkel |
| 5,713,844 A | 2/1998 | Peyman |
| 5,843,111 A | 12/1998 | Vijfvinkel |
| 5,868,697 A | 2/1999 | Richter et al. |
| 5,948,427 A | 9/1999 | Yamamoto et al. |
| 6,099,522 A | 8/2000 | Knopp et al. |
| 6,102,045 A | 8/2000 | Nordquist et al. |
| 6,120,147 A | 9/2000 | Vijfvinkel et al. |
| 6,142,990 A | 11/2000 | Burk |
| 6,220,247 B1 | 4/2001 | Maldanado Bas |
| 6,241,721 B1 | 6/2001 | Cozean et al. |
| 6,375,642 B1 | 4/2002 | Grieshaber et al. |
| 6,383,219 B1 | 5/2002 | Telandro et al. |
| 6,450,984 B1 | 9/2002 | Lynch et al. |
| 6,464,724 B1 | 10/2002 | Lynch et al. |
| 6,494,857 B1 | 12/2002 | Neuhann |
| 6,524,275 B1 | 2/2003 | Lynch et al. |
| 6,533,768 B1 | 3/2003 | Hill |
| 6,544,249 B1 | 4/2003 | Yu et al. |
| 6,607,542 B1 | 8/2003 | Wild |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,211 B2 | 3/2004 | Savage |
| 6,726,676 B2 | 4/2004 | Steggman et al. |
| 6,730,056 B1 | 5/2004 | Ghaem et al. |
| 6,736,791 B1 | 5/2004 | Tu et al. |
| 6,764,439 B2 | 7/2004 | Schaaf et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,939,298 B2 | 9/2005 | Brown et al. |
| 6,939,341 B2 | 9/2005 | Vijfvinkel |
| 6,955,656 B2 | 10/2005 | Bergheim et al. |
| 6,979,328 B2 | 12/2005 | Baerveldt et al. |
| 6,981,958 B1 | 1/2006 | Gharib et al. |
| 7,094,225 B2 | 8/2006 | Tu et al. |
| 7,118,547 B2 | 10/2006 | Dahan |
| 7,135,009 B2 | 11/2006 | Tu et al. |
| 7,135,016 B1 | 11/2006 | Asia et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,338,477 B2 | 3/2008 | Meyer et al. |
| 7,431,710 B2 | 10/2008 | Tu et al. |
| 7,458,953 B2 * | 12/2008 | Peyman .......................... 604/9 |
| 7,488,303 B1 | 2/2009 | Haffner et al. |
| 7,557,087 B2 | 7/2009 | Rothbard et al. |
| 7,563,241 B2 | 7/2009 | Tu et al. |
| 7,678,065 B2 | 3/2010 | Haffner et al. |
| 7,699,882 B2 | 4/2010 | Stamper et al. |
| 7,708,711 B2 | 5/2010 | Tu et al. |
| 7,740,604 B2 | 6/2010 | Schieber et al. |
| 7,785,321 B2 | 8/2010 | Baerveldt et al. |
| 7,803,558 B2 | 9/2010 | Stamer et al. |
| 7,850,637 B2 | 12/2010 | Lynch et al. |
| 7,857,782 B2 | 12/2010 | Tu et al. |
| 7,867,186 B2 | 1/2011 | Haffner et al. |
| 7,867,205 B2 | 1/2011 | Bergheim et al. |
| 7,879,001 B2 | 2/2011 | Haffner et al. |
| 7,879,079 B2 | 2/2011 | Tu et al. |
| 7,886,747 B2 | 2/2011 | Slatkine et al. |
| 7,909,789 B2 | 3/2011 | Badawi et al. |
| 7,931,596 B2 | 4/2011 | Rachlin et al. |
| 7,951,155 B2 | 5/2011 | Smedley et al. |
| 7,959,641 B2 | 6/2011 | Sorensen et al. |
| 7,967,772 B2 | 6/2011 | McKenzie et al. |
| 8,007,459 B2 | 8/2011 | Haffner et al. |
| 8,034,105 B2 | 10/2011 | Stegmann et al. |
| 8,062,244 B2 | 11/2011 | Tu et al. |
| 8,070,290 B2 | 12/2011 | Gille et al. |
| 8,075,511 B2 | 12/2011 | Tu et al. |
| 8,109,896 B2 | 2/2012 | Nissan et al. |
| 8,118,768 B2 | 2/2012 | Tu et al. |
| 2002/0013546 A1 | 1/2002 | Grieshaber et al. |
| 2002/0072673 A1 | 6/2002 | Yamamoto et al. |
| 2002/0165478 A1 | 11/2002 | Gharib et al. |
| 2004/0193262 A1 | 9/2004 | Shadduck |
| 2004/0254520 A1 | 12/2004 | Porteous et al. |
| 2004/0260228 A1 | 12/2004 | Lynch et al. |
| 2005/0090807 A1 | 4/2005 | Lynch et al. |
| 2005/0119601 A9 | 6/2005 | Lynch et al. |
| 2005/0192527 A1 * | 9/2005 | Gharib et al. .................... 604/8 |
| 2005/0244464 A1 | 11/2005 | Hughes |
| 2006/0149194 A1 | 7/2006 | Conston et al. |
| 2006/0195187 A1 | 8/2006 | Stegmann et al. |
| 2007/0179471 A1 | 8/2007 | Christian et al. |
| 2008/0077120 A1 | 3/2008 | Vijfvinkel |
| 2008/0097420 A1 | 4/2008 | Vijfvinkel et al. |
| 2009/0036878 A1 | 2/2009 | Vijfvinkel et al. |
| 2009/0043321 A1 | 2/2009 | Conston et al. |
| 2009/0082860 A1 | 3/2009 | Schieber et al. |
| 2009/0082862 A1 | 3/2009 | Schieber et al. |
| 2009/0132040 A1 | 5/2009 | Frion et al. |
| 2009/0227934 A1 | 9/2009 | Euteneuer et al. |
| 2010/0010414 A1 | 1/2010 | Bergheim et al. |
| 2010/0106073 A1 | 4/2010 | Haffner et al. |
| 2010/0121342 A1 | 5/2010 | Schieber et al. |
| 2010/0134759 A1 | 6/2010 | Silvestrini et al. |
| 2010/0179652 A1 | 7/2010 | Yamamoto et al. |
| 2010/0189765 A1 * | 7/2010 | Erickson et al. .............. 424/427 |
| 2010/0191329 A1 | 7/2010 | Badawi et al. |
| 2010/0222733 A1 | 9/2010 | Schieber et al. |
| 2010/0240987 A1 | 9/2010 | Christian et al. |
| 2011/0009874 A1 | 1/2011 | Wardle et al. |
| 2011/0009958 A1 | 1/2011 | Wardle et al. |
| 2011/0015658 A1 | 1/2011 | Vijfvinkel |
| 2011/0098809 A1 | 4/2011 | Wardle et al. |
| 2011/0118711 A1 | 5/2011 | Vijfvinkel et al. |
| 2011/0130831 A1 | 6/2011 | Badawi et al. |
| 2011/0196487 A1 | 8/2011 | Badawi et al. |
| 2011/0319806 A1 | 12/2011 | Wardle |
| 2012/0010702 A1 | 1/2012 | Stegmann et al. |

FOREIGN PATENT DOCUMENTS

| | | |
|---|---|---|
| WO | WO 2005/094742 | 10/2005 |
| WO | WO 2009/120075 | 10/2009 |
| WO | WO 2010/077136 | 7/2010 |
| WO | WO 2011/081525 | 7/2011 |
| WO | WO 2011/105909 | 9/2011 |

* cited by examiner

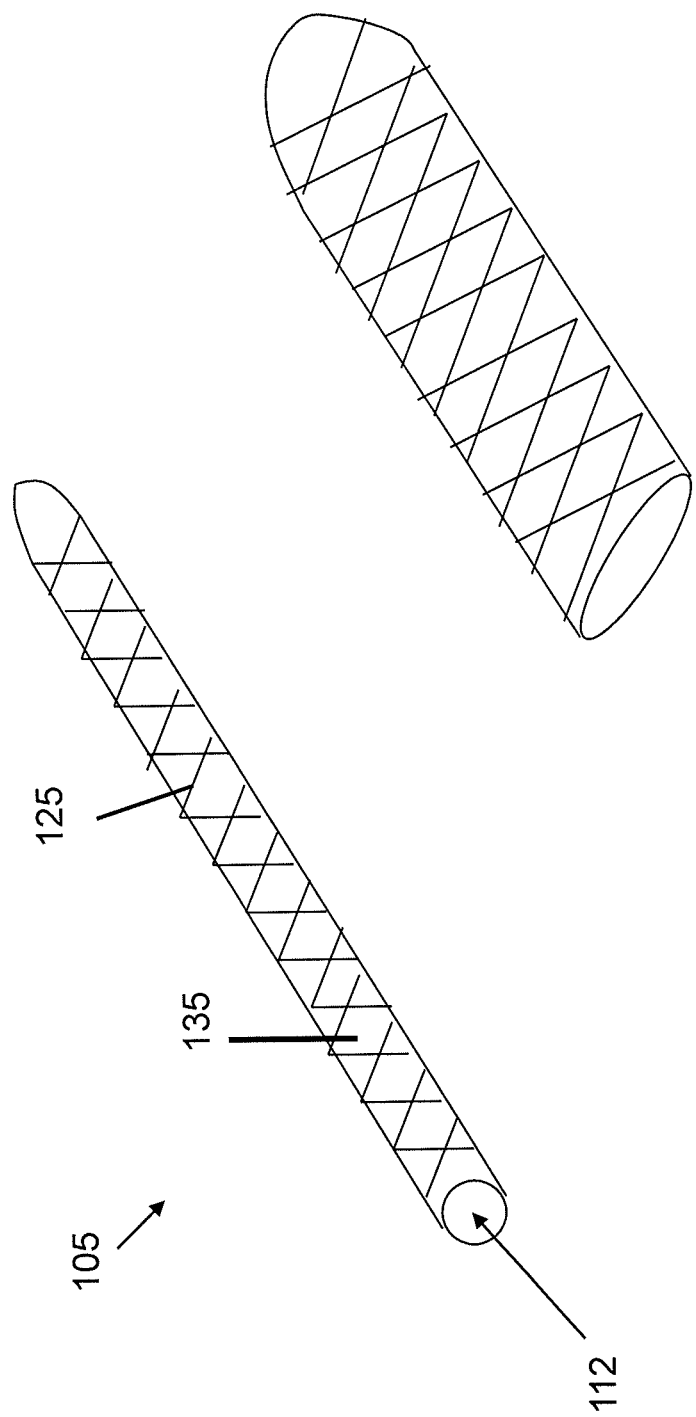

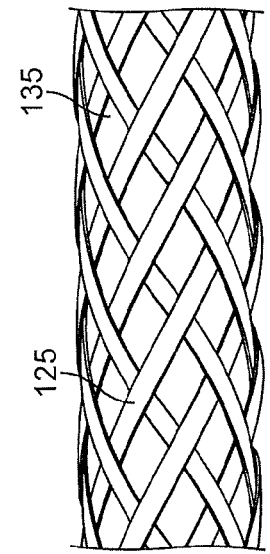
FIG. 3C
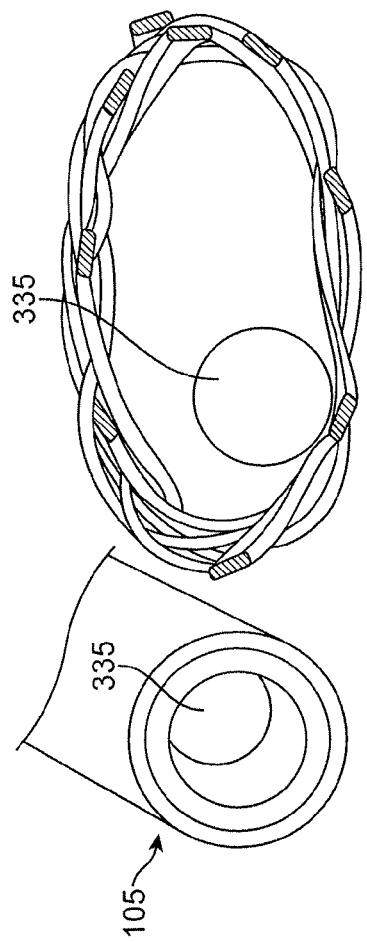
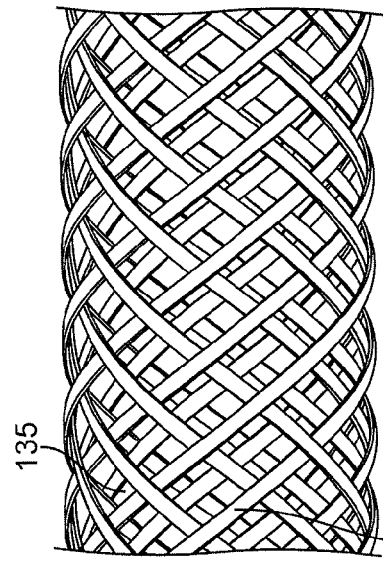
FIG. 3D
FIG. 3E

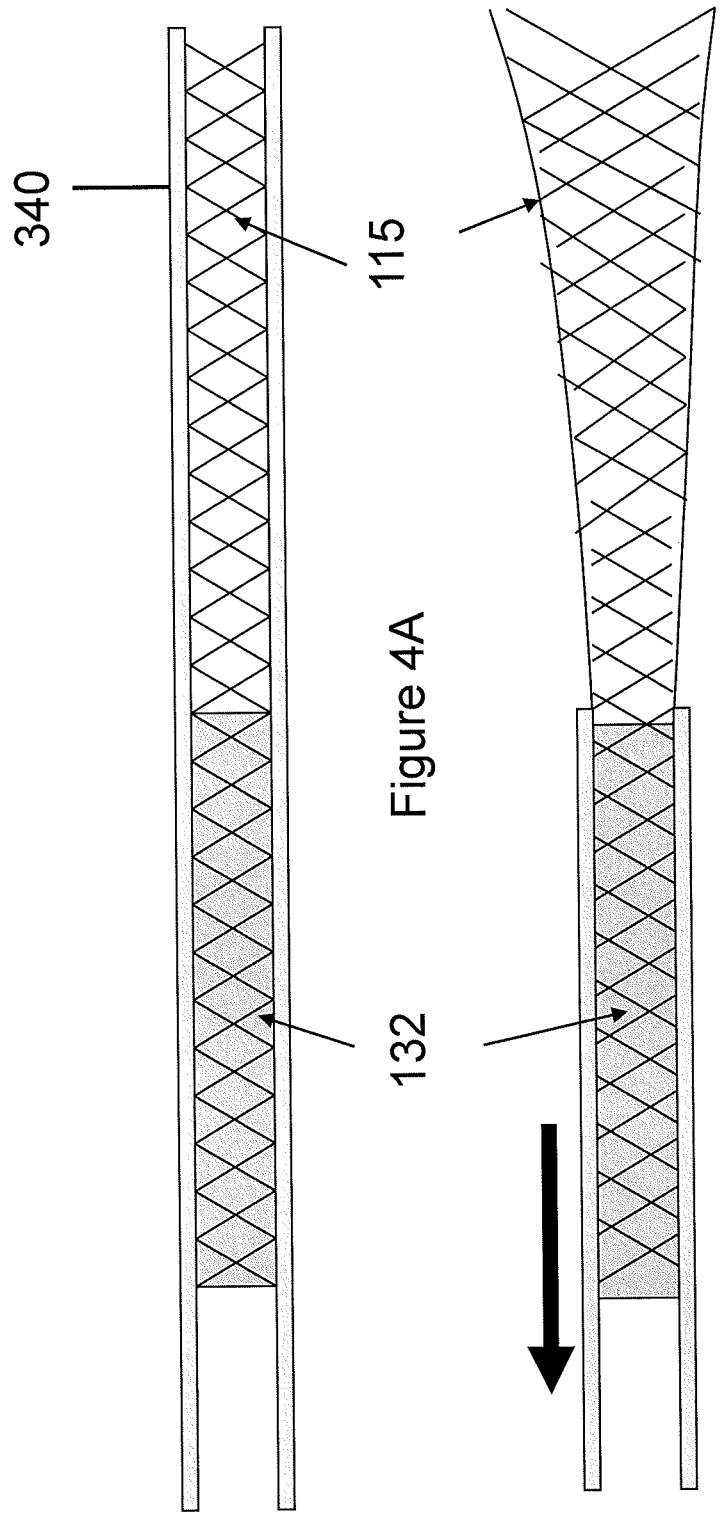

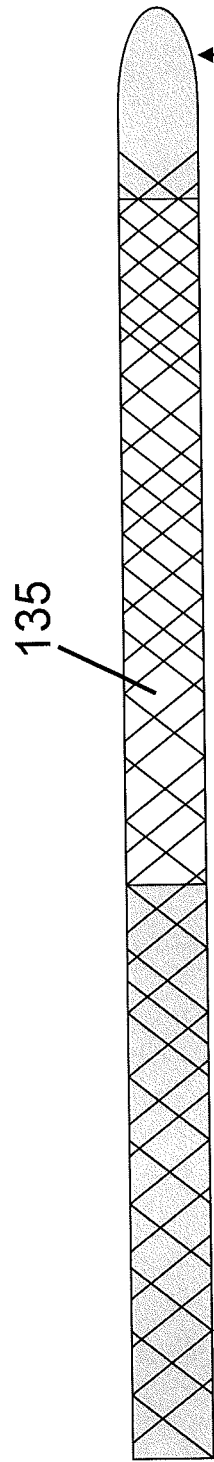
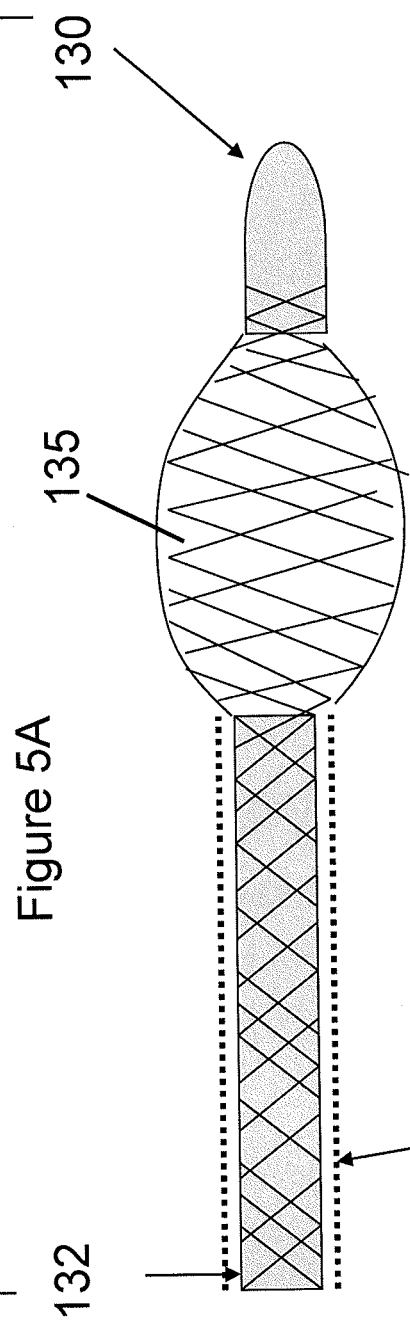
Figure 5A
Figure 5B

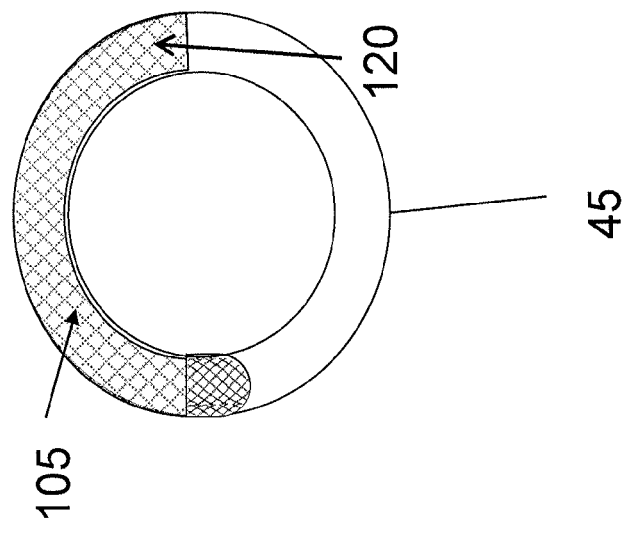
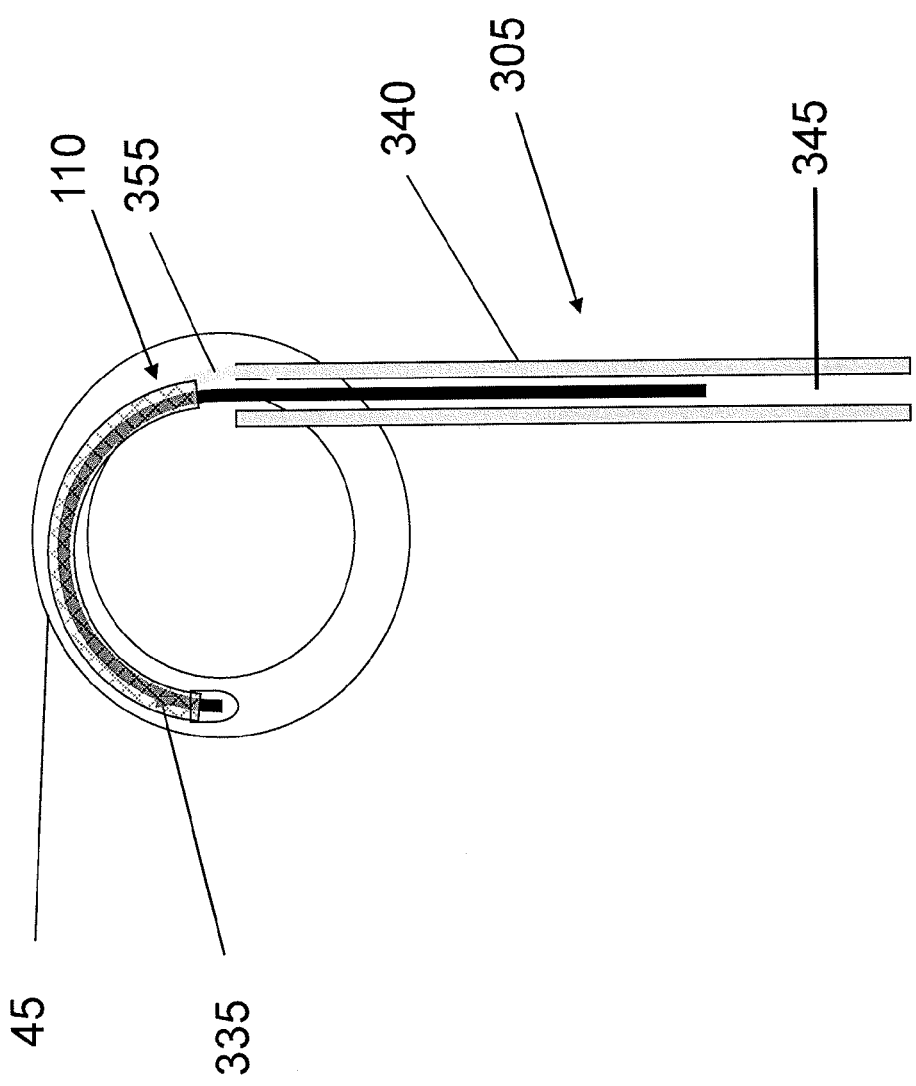

EXPANDABLE OCULAR DEVICES

REFERENCE TO PRIORITY DOCUMENT

This application claims priority of U.S. Provisional Patent Application Ser. No. 61/353,162, entitled "Expandable Ocular Devices" by Thomas A. Silvestrini, filed Jun. 9, 2010. Priority of the filing date of Jun. 9, 2010, is hereby claimed, and the disclosure of the provisional patent application is hereby incorporated by reference in its entirety.

BACKGROUND

The mechanisms that cause glaucoma are not completely known. It is known that glaucoma results in abnormally high pressure in the eye, which leads to optic nerve damage. Over time, the increased pressure can cause damage to the optic nerve, which can lead to blindness. Treatment strategies have focused on keeping the intraocular pressure down in order to preserve as much vision as possible over the remainder of the patient's life.

Past treatment includes the use of drugs that lower intraocular pressure through various mechanisms. The glaucoma drug market is an approximate two billion dollar market. The large market is mostly due to the fact that there are not any effective surgical alternatives that are long lasting and complication-free. Unfortunately, drug treatments as well as surgical treatments that are available need much improvement, as they can cause adverse side effects and often fail to adequately control intraocular pressure. Moreover, patients are often lackadaisical in following proper drug treatment regimens, resulting in a lack of compliance and further symptom progression.

With respect to surgical procedures, one way to treat glaucoma is to implant a drainage device in the eye. The drainage device functions to drain aqueous humor from the anterior chamber and thereby reduce the intraocular pressure. The drainage device is typically implanted using an invasive surgical procedure. Pursuant to one such procedure, a flap is surgically formed in the sclera. The flap is folded back to form a small cavity and the drainage device is inserted into the eye through the flap. Such a procedure can be quite traumatic as the implants are large and can result in various adverse events such as infections and scarring, leading to the need to re-operate.

In view of the foregoing, there is a need for improved devices and methods for the treatment of glaucoma.

SUMMARY

Disclosed are devices, systems and methods of using an expandable ocular devices inserted ab interno to affect aqueous humor outflow from the anterior chamber for reducing elevated intraocular pressure.

In one aspect, disclosed is a system for treating an ocular disorder in an eye. The system includes an ocular device having a proximal end, a distal end, and an internal lumen forming a flow pathway extending from the proximal end to the distal end; at least one inflow region that communicates with the flow pathway; and an expandable portion having a plurality of interconnected struts forming multiple openings in the device communicating with the flow pathway. The expandable portion has a first cross-sectional shape suitable for insertion into the eye that is generally cylindrical and a second cross-sectional shape that is larger than the first cross-sectional shape. The system also includes a delivery device for inserting the ocular device into an eye. The system has a sheath configured to surround at least a portion of the ocular device; an applier configured to insert into the internal lumen of the ocular device; and an actuator.

The second cross-sectional shape of the ocular device can be oval. The expandable portion of the ocular device can be located near the distal end and the second cross-sectional shape of the ocular device can be funnel-shaped. The interconnected struts of the ocular device can be braided or woven. The ocular device can include a tube having cut-outs forming the interconnected struts. The second cross-sectional shape of the ocular device can be between about 75% and about 100% larger than the first cross-sectional shape. The ocular device can approach a curvature of a region of the eye. At least a portion of the ocular device can be coated with a flexible material. The expandable portion of the ocular device can be self-expanding or actively expanded. The expandable portion can be actively expanded with a balloon coupled to the applier. The ocular device can be positioned in the eye such that the inflow region communicates with the anterior chamber. One or more of the openings can communicate with at least one tissue structure near an anterior angle of the eye such as the trabecular meshwork, juxtacanalicular structure, aqueous vein, episcleral vien, Schlemm's canal, a collecting channel, sclera, supraciliary space and suprachoroidal space. The ocular device can conform to a contour of the tissue structure surrounding the ocular device. The expandable portion can be configured to expand or stretch the tissue structure. The ocular device can be advanced around Schlemm's canal up to about 340 degrees. The ocular device can have a length that extends from the anterior chamber to a portion of Schlemm's canal. The flow of aqueous humor can occur from the anterior chamber into the flow pathway and through one or more openings in the ocular device. The distal end of the ocular device can be closed. The distal end of the ocular device can be permanently coupled to the applier such that the ocular device is not releasably deployed within the eye. Following expansion to the second cross-sectional shape the expandable portion can be returned to the first cross-sectional shape and removed from the eye.

In another aspect, disclosed is a method for the surgical treatment of an ocular disorder in an eye. The method includes coupling an ocular stent device to a delivery device having an applier, a sheath, and an actuator. The method also includes forming an incision in the cornea and introducing the ocular stent device into the anterior chamber of the eye through the incision using the delivery device. The ocular stent device includes a proximal end, a distal end, and an internal lumen forming a flow pathway extending from the proximal end to the distal end; an inflow region near the proximal end communicating with the flow pathway; and an expandable region having a plurality of interconnected struts forming multiple openings communicating with the flow pathway. The expandable region has a first cross-sectional shape suitable for insertion into the eye that is generally cylindrical and a second cross-sectional shape that is larger than the first cross-sectional shape. The method also includes inserting the distal end of the ocular stent device into a tissue structure near an anterior angle of the eye such that the inflow region remains in communication with the anterior chamber and at least a portion of the expandable region is positioned within the tissue structure; expanding the expandable region; and conducting aqueous humor from the anterior chamber towards the tissue structure.

Expanding the expandable region can include uncoupling the delivery device from the ocular stent device allowing the expandable region to passively expand. Expanding the expandable region can include actively expanding the expandable region with the delivery device. The second cross-sectional shape can be a generally oval shape. The second cross-sectional shape can be a funnel shape. Inserting the distal end of the ocular stent device into the tissue structure can include inserting the distal end of the ocular stent device into at least one of a trabecular meshwork, juxtacanalicular structure, collecting channel, aqueous vein, episcleral vein, Schlemm's canal, sclera, supraciliary space and suprachoroidal space. The method can also include returning the expandable region to the first cross-sectional shape. The method can also include removing the ocular stent device from the eye. The tissue structure can be maintained in an expanded configuration after removal of the ocular stent device from the eye. Inserting the distal end of the ocular stent device into the tissue structure can also include creating an opening in the tissue structure.

More details of the devices, systems and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

FIGS. 3A-3B show schematic views of an embodiment of a device transitioning from an insertion configuration to a deployed configuration;

FIGS. 3C-3E show front, top and side views of an embodiment of a device having a circular insertion configuration and an oval deployed configuration;

FIGS. 4A-4B show another embodiment of a device having a tulip-shaped deployed configuration;

FIGS. 5A-5B show schematic views of an embodiment of a device transitioning between an insertion configuration and a deployed configuration;

FIGS. 9A-9B show schematic views of an instrument inserting a device into Schlemm's canal.

It should be appreciated that the drawings herein are exemplary only and are not meant to be to scale.

DETAILED DESCRIPTION

There is a need for improved methods and devices for the treatment of eye diseases. Disclosed herein are low profile, simplified devices and methods of use that can be used in the eye for the treatment of glaucoma and other eye diseases. The devices described herein can be inserted ab interno and in a manner that stretches, expands, restores, creates and/or maintains an opening in the eye. The tissue location of implantation of the devices described herein can vary and include at least the trabecular meshwork, juxtacanalicular trabecular meshwork, Schlemm's canal, collecting channel, episcleral vein, aqueous vein, sclera, supraciliary space, suprachoroidal space or other locations in the eye to maintain, facilitate and/or improve flow of aqueous humor out from the anterior chamber and reduce elevated intraocular pressure. For example, the devices described herein can be used to insert through the trabecular meshwork to Schlemm's canal where the device can be expanded to stretch and open the canal. The devices described herein also can be used to create and maintain a separation between tissues such between the ciliary body and the sclera forming a supraciliary space, or between the choroid and the sclera forming a suprachoroidal space.

Figure 1A:
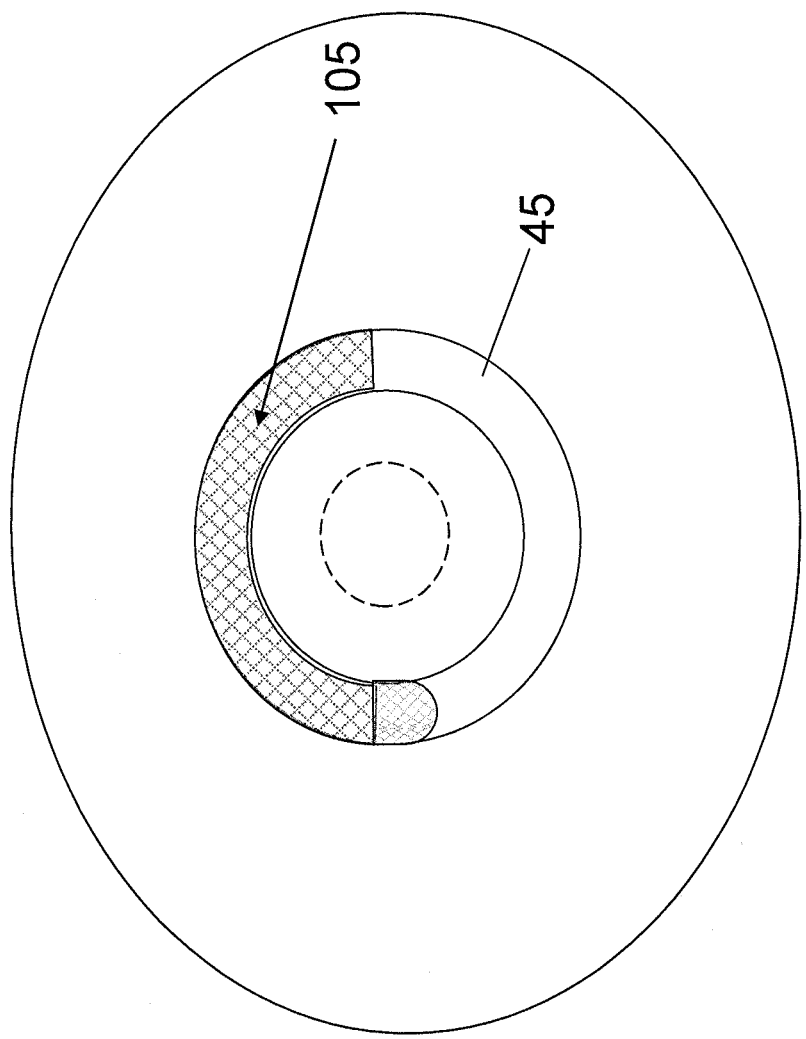
FIG. 1A shows a top plan view of an embodiment of a device positioned within a portion of Schlemm's canal.

In some embodiments, the devices described herein can be placed in the eye such that the device improves flow or drainage of aqueous humor from the anterior chamber to Schlemm's canal. FIG. 1A shows a top plan view of a device 105 positioned within a portion of Schlemm's canal 45. In some embodiments, the devices described herein can be used to create and maintain an opening in the trabecular meshwork. The devices described herein can also be reversibly and temporarily expanded to stretch and create expanded regions within the eye that are maintained even after removal of the device. Aqueous humor can flow from the anterior chamber towards tissues and tissue structures that are separated, stretched, expanded and/or held open by the devices described herein as will be discussed in more detail below such that flow through the structure or towards another region of the eye is maintained, facilitated or improved.

Eye Anatomy and Glaucoma

Figure 1B:
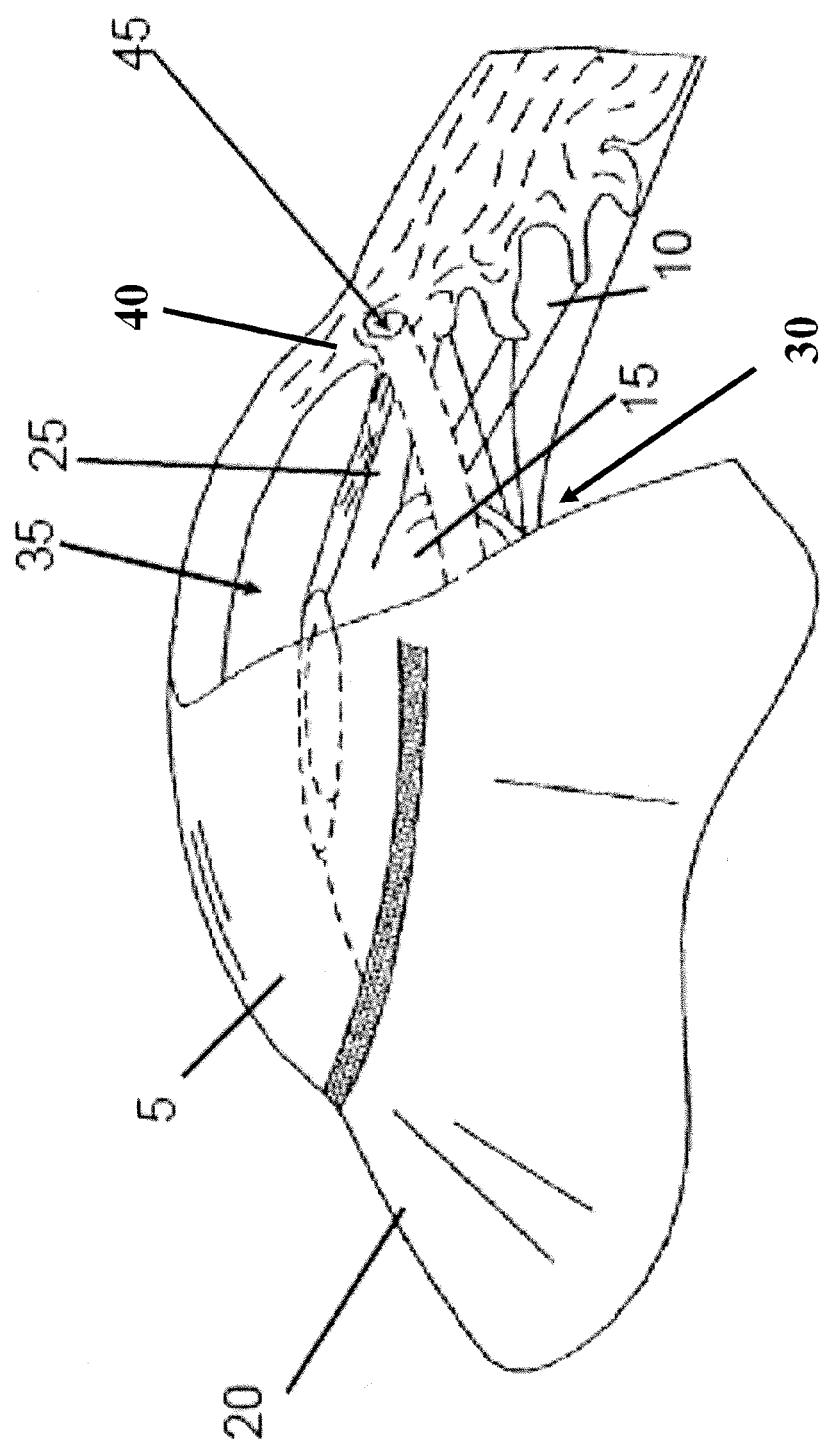
FIG. 1B shows a 3-D sectional view indicating the traverse of Schlemm's canal around the limbus.

As shown in FIG. 1B, the eye is generally spherical and is covered on the outside by the sclera 20. The retina (not shown) lines the inside posterior half of the eye and registers the light and sends signals to the brain via the optic nerve. The bulk of the eye is filled and supported by the vitreous body, a clear, jelly-like substance. The elastic lens 15 is located near the front of the eye. The lens 15 provides adjustment of focus and is suspended within a capsular bag from the ciliary body 10, which includes the muscles that change the focal length of the lens 15. A volume in front of the lens 15 is divided into two by the iris 25, which controls the aperture of the lens 15 and the amount of light striking the retina. The pupil is a hole in the center of the iris 25 through which light passes. The volume between the iris 25 and the lens 15 is the posterior chamber 30. The volume between the iris 25 and the cornea 5 is the anterior chamber 35. Both chambers are filled with a clear liquid known as aqueous humor.

The ciliary body 10 continuously forms aqueous humor in the posterior chamber 30. The aqueous humor flows around the lens 15 and iris 25 into the anterior chamber 35 and can exit the eye through the trabecular meshwork 40, a sieve-like structure situated at the corner of the iris 25 and the wall of the eye (the corner is known as the iridocorneal angle). Some of the aqueous humor filters through the trabecular meshwork 40 into Schlemm's canal 45, a small channel that drains into the ocular veins. The excess aqueous humor enters the venous blood stream from Schlemm's canal 45 and is carried along with the venous blood leaving the eye. A smaller portion of the aqueous humor from the anterior chamber 35 rejoins the venous circulation after passing through the muscle fibers of the ciliary body 10 and eventually out from the eye through the sclera 20 (the uveoscleral route).

Glaucoma is a disease wherein the aqueous humor builds up within the eye. In a healthy eye, the ciliary processes secrete aqueous humor, which then passes through the angle as described above. Glaucoma appears to be the result of clogging in the trabecular meshwork. The clogging can be caused by the exfoliation of cells or other debris. When the aqueous humor does not drain properly from the clogged meshwork, it builds up and causes increased pressure in the eye, particularly on the blood vessels that lead to the optic nerve. The high pressure on the blood vessels can result in death of retinal ganglion cells and eventual blindness.

Closed angle (acute) glaucoma can occur in people who were born with a narrow angle between the iris and the cornea (the anterior chamber angle). This is more common in people who are farsighted (they see objects in the distance better than those which are close up). The iris can slip forward and suddenly close off the exit of aqueous humor, and a sudden increase in pressure within the eye follows.

Open angle (chronic) glaucoma is by far the most common type of glaucoma. In open angle glaucoma, the iris does not block the drainage angle as it does in acute glaucoma. Instead, the fluid outlet channels within the wall of the eye gradually narrow with time. The disease usually affects both eyes, and over a period of years the consistently elevated pressure slowly damages the optic nerve.

Devices

Figure 2A:
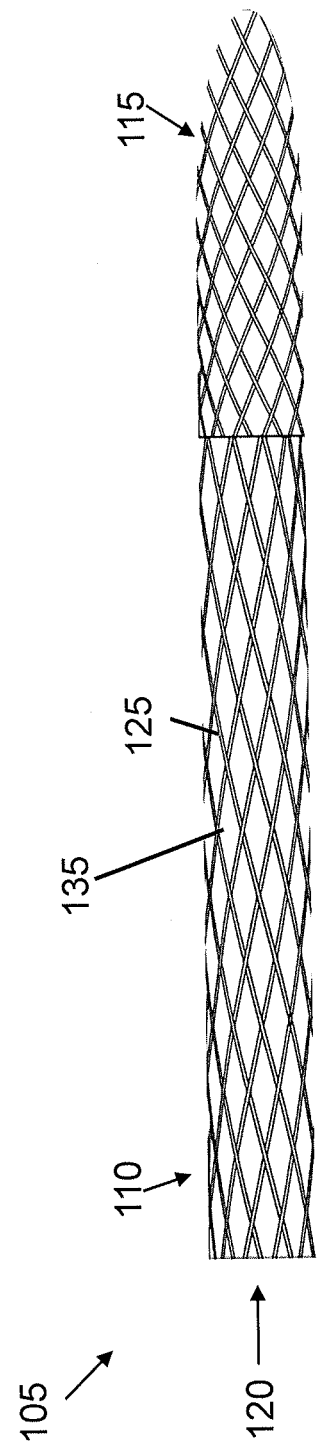
FIG. 2A shows a schematic view of one embodiment of a device.
Figure 2B:
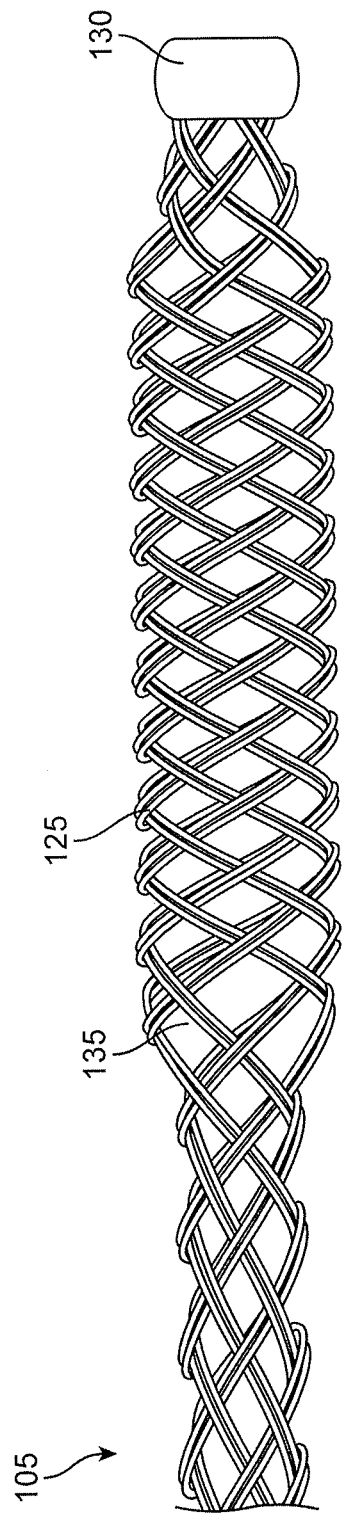
FIG. 2B shows a top view of another embodiment of a device.

FIG. 2A shows one variation of a device 105 in schematic and FIG. 2B shows another variation of a device 105. The device 105 can be a generally elongate member having a proximal end 110, a distal end 115 and an inner passageway 120 that can be expanded upon implantation in the eye. The proximal end 110 can have an inlet 112 to the inner passageway 120 permitting fluid (such as aqueous humor) to flow through the device 105. The inner passageway 120 can also be used to mount the device 105 onto a delivery system, as described below. The device 105 can be formed by a plurality of intertwining or interconnected struts 125. The struts 125 can form multiple openings 135 in the body of the device 105. The flow of aqueous through the device 105 can occur through the plurality of openings 135 such that flow of aqueous humor can occur in more than a single direction.

The device 105 can have a substantially uniform diameter along its entire length, although the shape of the device 105 can vary along its length (either before or after insertion of the device), as described below. Moreover, the device 105 can have various cross-sectional shapes (such as circular, oval, triangular or rectangular or other shape) and can vary in cross-sectional shape moving along its length. The cross-sectional shape can change between a first shape that can facilitate or increase the ease of insertion into the eye and a second shape that can be optimized for deployment within a structure of the eye as will be discussed in more detail below.

The device 105 can be formed by a plurality of intertwining or interconnected strands or struts 125. The struts 125 can be interconnected such as in a twisted, braided, or woven fashion. The device 105 can also be a laser cut tube, for example a stent made of stainless steel or a shape-memory metal such as Nitinol. The multiple openings 135 can be created in the tube as opposed to being provided by the negative space between interconnected strands. The device 105 can also be a combination of braided portions and solid portions. For example, the distal end 115 of the device 105 can be sealed such that a solid tip 130 is formed (see FIG. 2B). Similarly, the proximal end 110 of the device 105 can be reinforced with a solid material 132 (see FIGS. 4A-4B and 5A-5B). The device 105 can also be coated with a flexible material along part or all of its length. Variations in open and solid portions along the length of the device 105 can provide the device 105 with various expanded configurations when deployed in the eye.

The braided sections of the device 105 provide the device with a structure that can be expanded once the device is positioned within the device site in the eye. In the first, insertion configuration the device 105 can have a narrow or relatively small outer diameter that is optimized for ab interno insertion in the eye. In the second configuration the device 105 can expand to a larger diameter such that it is optimized for deployment and expansion within a target tissue location in the eye, such as Schlemm's canal, trabecular meshwork, juxtacanalicular trabecular meshwork, collecting channel, episcleral vein, aqueous vein, sclera, supraciliary space, suprachoroidal space or another location in the eye.

The cross-sectional shape of the device 105 in the insertion configuration can be different from the cross-sectional shape of the device in the deployment configuration. For example, the device 105 can have a circular cross-sectional shape in the insertion configuration and an oval cross-sectional shape in the deployment configuration. FIGS. 3A-3B show schematic views of a device 105 that can transition from a circular cross-sectional shape to an oval cross-sectional shape. FIG. 3C shows a side-by-side comparison of the device 105 showing the circular cross-sectional shape (left side) of the insertion configuration and the oval cross-sectional shape (right side) of the deployed configuration. A guide wire 335 is shown inserted through the internal passageway 120 of the device 105. FIG. 3D show a top view of the device 105 and FIG. 3E shows the device 105 from the side.

The cross-sectional shape of the device 105 can be selected and optimized depending on where in the eye the device 105 will be deployed. For example, the oval shape of the device 105 can more closely conform to the contour of Schlemm's canal 45 and can be further stabilizing with respect to the iris and cornea and prevent rotation of the device 105. In another variation, the distal end 115 of the device 105 can expand to a greater degree than the more proximal regions of the device 105 such that the expanded device has a tulip or funnel shape as shown in FIGS. 4A-4B.

The device 105 can be self-expanding or can be actively expanded such as with a balloon catheter or other activation mechanism. The device 105 can be biased toward an expanded state. For example as shown in FIGS. 4A-4B, the device 105 can be positioned within an outer sheath or introducer tube 340 or other structure that can constrain the device 105 into a state of reduced diameter prior to insertion. When the device 105 is positioned in the desired location in the eye, the device 105 can be released from such constraints, such as upon withdrawal of a guide wire 335 and/or the introducer tube 340, so that the device 105 is free to expand outward. The device 105 can be self-expanding or incorporate a shape-memory material. Alternatively, the device 105 can be actively expanded using one or more features of the delivery device. Delivery of the devices described herein will be discussed in more detail below.

The device 105 can include features such as one or more markers or sensors that can assist the user in positioning the device in a desired region of the eye. The features can be placed in one or more locations anywhere along the length of the device 105. The features can include, but are not limited to visual markers such as alignment marks, tabs, slots as well as one or more tomographic, echogenic, or radiopaque markers. The features can provide feedback to the user on placement, confirmation of placement or during patient follow-up. The features can signal in real-time the placement of the desired portion of the device 105 within a target location. For example, an echogenic marker can signal under ultrasound the placement of the device within the target location. In some embodiments, the features can allow the user to know alignment of the device 105 with respect to the delivery device. Other visualization features are described below.

In some embodiments of use, the device 105 can be inserted in the target location until a first marker is aligned with a relevant anatomic structure. For example, a marker on the device 105 can be tracked by a user as the device 105 is inserted ab interno through the anterior chamber toward the trabecular meshwork. The user can insert an appropriate length of the device 105 through the trabecular meshwork until the user can visually identify the marker is aligned with a particular anatomical structure in the eye. The marker alignment can indicate an appropriate length of the device 105 is inserted within the trabecular meshwork 40 and/or remains in the anterior chamber 35.

When positioned in the eye, the device 105 can be positioned within the trabecular meshwork 40 or juxtacanalicular trabecular meshwork 50 near the angle of the eye such that the inlet 112 near the proximal end 110 of the device is maintained within the anterior chamber 35. In some embodiments, a first portion of the device 105 can be positioned within the trabecular meshwork 40 and another portion of the device 105 can be positioned outside the trabecular meshwork 40. In some embodiments, the openings 135 of the device 105 are positioned such that aqueous humor from the anterior chamber can bypass the trabecular meshwork 40 and flow into Schlemm's canal 45. In some embodiments, the distal end 115 of the device 105 can extend into Schlemm's canal 45 or another tissue structure in the eye up to the level of the aqueous veins. In some embodiments, the device can expand into an oval, circular or semi-circular cross-sectional shape. In some embodiments, the cross-sectional shape of the device is configured to expand the general circumference of the surrounding tissues.

Expansion of the device 105 into its deployed configuration can act to expand the surrounding tissues. In some embodiments, the deployed configuration of the device 105 can maintain the patency or expand at least a portion of the lumen of the Schlemm's canal 45, trabecular meshwork 40 and/or juxtacanalicular trabecular meshwork 50. The device 105 generally avoids expanding certain tissues or expanding tissues to a degree that the device negatively impacts flow through the surrounding tissues. For example, expansion of the device 105 in Schlemm's canal 45 does not significantly impact the normal flow of fluid through the trabecular meshwork 40.

It should be appreciated that the configuration of the devices described herein can vary. For example, the device can be an elongate element having a substantially uniform diameter along its entire length. In some embodiments, the device has an outer diameter that can be or can expand to be at least about 50 microns, 60 microns, 70 microns, 80 microns, 90 microns, 100 microns, 150 microns, 200 microns, 250 microns, 300 microns, 350 microns, 400 microns or larger. In some embodiments, the outer diameter of the device in the expanded configuration can be at least about 50%, 75%, 80%, 85%, 90%, 95%, 100%, 125%, 150%, or 200% greater than the outer diameter of the device in insertion configuration.

In some embodiments, the outer diameter of the device in the expanded configuration can be at least about 50%, 75%, 80%, 85%, 90%, 95%, 100%, 125%, 150%, or 200% greater than a physiological size of a tissue structure, channel or space, such as the diameter of Schlemm's canal. In some embodiments, the device has an outer diameter substantially equal to the size of Schlemm's canal. In some embodiments, the device can be expandable to a shape having an outer diameter that is larger than the diameter of Schlemm's canal. In some embodiments, the device can be advanced into and expanded around Schlemm's canal 45. In some embodiments, the device 105 can expand around Schlemm's canal 45 up to about 340 degrees.

In some embodiments, the device has an inner diameter in the range of about 0.002 inches to about 0.050 inches, an outer diameter in the range of about 0.006 inches to about 0.100 inches, and a length in the range of about 0.100 inches to about 1.50 inches. In other embodiments, the device has an inner diameter in the range of about 0.008 inches to about 0.025 inches. In other embodiments, the device has an inner diameter in the range of about 0.010 inches to about 0.012 inches. In other embodiments, the device has an outer diameter in the range of about 0.012 inches to about 0.075 inches. In other embodiments, the device has an outer diameter in the range of about 0.025 inches to about 0.050 inches. In other embodiments, the device has a length in the range of about 0.125 inches to about 0.75 inches. In other embodiments, the device has a length in the range of about 0.25 inches to about 0.50 inches. In other embodiments, the device has an inner diameter of about 0.012 inches, an outer diameter of about 0.020 inches and a length of about 0.25 inches.

It should be appreciated that the devices may or may not have a lumen or internal or external channels for transport of aqueous humor. For example, the device can have a solid body that does not include a flow channel. The device can have a thin, elongated structure, such as one or more fibers, filaments or monofilament wires of polymer. In some embodiments, the device can be a filament having a diameter of at least about 10 microns, 15 microns, 20 microns, 25 microns, 30 microns or larger.

The device can include a plurality of interconnected strands, such as in a twist or braid or other woven fashion. The device can also be repeatedly expanded and contracted to dilate portions of the canal during advancement into a tissue location in the eye. The device can be elongate and relatively flexible such that it can follow a particular curve-contour, such as the curve of Schlemm's canal or another curvature of a location in the eye, and can be expanded such that it can maintain that curve-contour once expanded to an enlarged shape.

The device 105 can have a stiffness that is greater than the stiffness of adjacent eye tissue such that the device 105 deforms the eye tissue. The device 105 can have an effective or extrinsic Young's modulus (relative to the Young's modulus of the tissue) that causes the device 105 to stretch, prop open or otherwise interfere with the normal shape of the structural feature within which it is implanted. The effective modulus of the device 105 can depend upon the intrinsic modulus (or Young's modulus in this case), the shape and thickness of the device. In some embodiments, the device 105 can be made of a material that has the requisite stiffness for expansion of a target tissue. In some embodiments, the device can have structural properties, such as thickness or length, that achieve the requisite stiffness for expanding the target tissues. In some embodiments, the device 105 can have column strength sufficient to permit the device 105 to be inserted, expanded and stretched within Schlemm's canal without structural collapse or structural degradation of the device 105.

In some embodiments, a portion of the device can be made of a material that has a Young's modulus that is between about 30,000 psi and about 70,000 psi. In other embodiments, the Young's modulus is between about 70,000 psi to about 200,000 psi. In other embodiments, the Young's modulus is between about 100,000 psi to about 200,000 psi. In other embodiments, the Young's modulus is approximately 200,000 psi. In other embodiments, the Young's modulus is less than or equal to 40,000,000 psi. It should be appreciated that the aforementioned values are for example and non-limiting. As mentioned above, the effective modulus of the device depends upon intrinsic modulus, or Young's modulus, shape and thickness of the device.

The device 105 can be made of various materials, including, for example, polyimide, titanium, tungsten, nickel-titanium alloys, cobalt-chrome alloys, Nitinol, platinum, stainless steel, molybdenum, or any other suitable polymer, metal, metal alloy, or ceramic biocompatible material or combinations thereof. The device can be configured from a piece of filament or wire, cut from a length of material with a desired cross-sectional configuration, chemically etched, mechanically or laser machined, extruded or molded. Other materials of manufacture or materials with which the device can be coated or manufactured entirely include silicone, PTFE, ePTFE, differential fluoropolymer, FEP, FEP laminated into nodes of ePTFE, silver coatings (such as via a CVD process), gold, prolene/polyolefins, polypropylene, poly(methyl methacrylate) (PMMA), acrylic, PolyEthylene Terephthalate (PET), Polyethylene (PE), PLLA, and parylene. The device 105 can be a braided or laser-cut device made of stainless steel or Nitinol. The device 105 can be reinforced with polymer, Nitinol, or stainless steel braid or coiling or can be a co-extruded or laminated tube with one or more materials that provide acceptable flexibility and hoop strength for adequate lumen support and drainage through the lumen. The device 105 can alternately be manufactured of nylon (polyamide), PEEK, polysulfone, polyamideimides (PAI), polyether block amides (Pebax), polyurethanes, thermoplastic elastomers (Kraton, etc), and liquid crystal polymers.

The device 105 can include one or more structural features that aid to position, anchor and/or retain the device 105 in one or more locations within the implantation site in the eye. The structural features can include flanges, protrusions, wings, tines, or prongs, and the like that can lodge into the surrounding eye anatomy. In some embodiments, expansion of the device causes the structural features to lodge into the anatomy to retain the device 105 in place and prevent the device 105 from moving from the implantation site. These structural features can also provide for regions of fibrous attachment between the device 105 and the surrounding eye anatomy. Fibrous attachment can result, for example, from endothelial cell growth in, around and/or between retention features and the struts 125 of the device 105. Alternatively, the device 105 can be coated with a material that prevents fibrous attachment to the device 105 and endothelial cell re-growth is avoided.

It should be appreciated that the device need not be releasably deployed in the eye. The device can be permanently coupled to a guide wire or catheter as is known in the art. These devices are not releasably deployed within the eye, but rather reversibly expanded and removed upon removal of the delivery device as will be discussed in more detail below. The device can be constructed of the same materials as the releasably deployed devices as described above. The device can also be constructed of materials such as those materials used in the construction of balloon catheters as is known in the art, including, but not limited to polyvinyl chloride (PVC), polyethylene (PE), cross-linked polyethylene, polyolefins, polyolefin copolymer (POC), polyethylene terephthalate (PET), nylon, polymer blends, polyester, polyimide, polyamides, polyurethane, silicone, polydimethylsiloxane (PDMS) and the like or combinations thereof. The device can be constructed of relatively inelastic polymers such as PE, POC, PET, polyimide or a nylon material or combinations thereof. The device can be constructed of relatively compliant, elastomeric materials including, but not limited to, a silicone, latex, or mylar elastomer. The device can be embedded with other materials such as for example, metal, Kevlar or nylon fibers. The device can be constructed of a thin, non-extensible polymer film such as polyester or other flexible thermoplastic or thermosetting polymer film.

Any of the embodiments of the devices described herein can be coated on an inner or outer surface with one or more drugs or other materials, wherein the drug or material maintains the patency of the lumen or encourages in-growth of tissue to assist with retention of the device within the eye. The drug can also be used for disease treatment. The device can also be coated on its inner or outer surface with a therapeutic agent, such as a steroid, an antibiotic, an anti-inflammatory agent, an anticoagulant, an antiglaucomatous agent, an anti proliferative, or any combination thereof. The drug or therapeutic agent can be applied in a number of ways as is known in the art. Also the drug can be embedded in another polymer (nonabsorbable or bioabsorbable) that is coated on the device. The device can also be covered or coated with a material (such as polyester, ePTFE (also known as GORETEX), PTFE that provides a surface to promote healing of the device into the surrounding tissue. In order to maintain a low profile, well-known sputtering techniques can be employed to coat the device. Such a low profile coating would accomplish a possible goal of preventing migration while still allowing easy removal if desired.

Delivery System

Figure 6A:
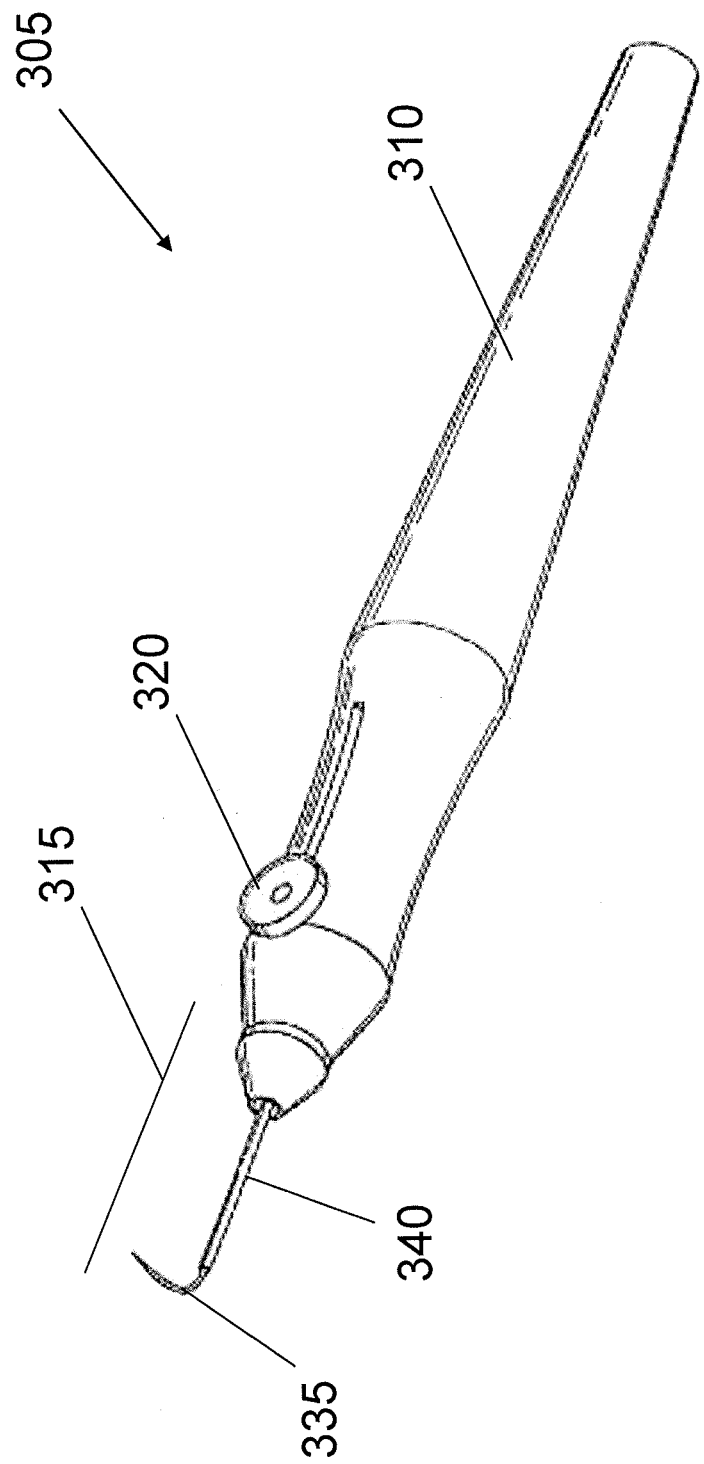
FIGS. 6A-6C show schematic views of an instrument for inserting a device.
Figure 6B:
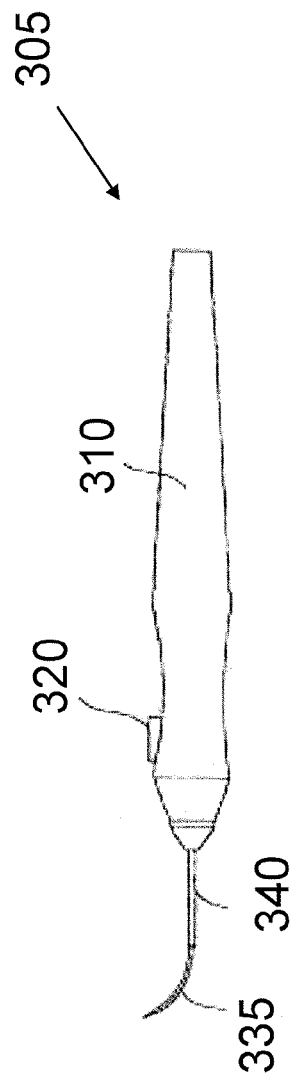
Figure 6C:
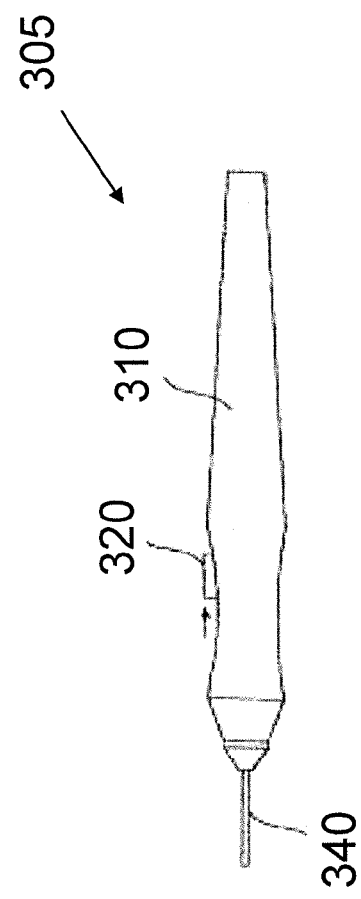

FIGS. 6A-6C show an embodiment of a delivery system 305 that can be used to deliver the device 105 into the eye. It should be appreciated that the delivery system 305 is for illustration and that variations in the structure, shape and actuation of the delivery system 305 are possible. The delivery system 305 generally includes a proximal handle component 310 and a distal delivery component 315. The proximal handle component 310 can include an actuator 320 to control the release of a device from the delivery component 315 into the target location in the eye. The proximal handle component 310 also can include a channel for insertion of an internal visualization system, such as a fiber optic image bundle. Such a delivery system having an internal visualization system need not be used in conjunction with a gonioscope or viewing lens.

Figure 7A:
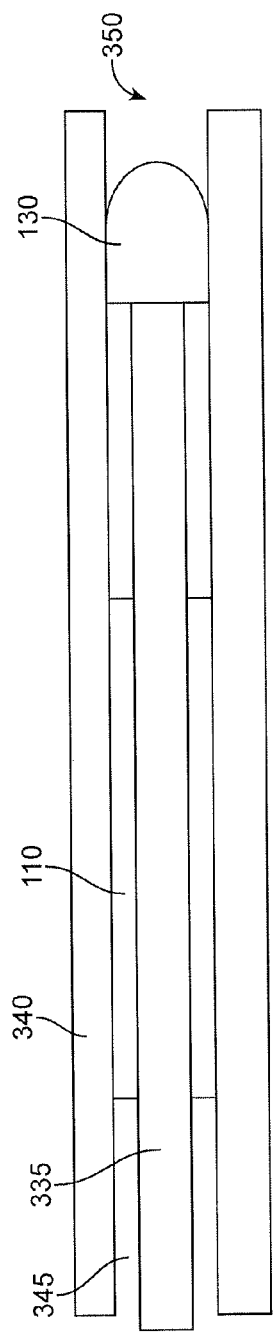
FIGS. 7A-7C show schematic views of a device being released from a delivery device.

The delivery component 315 can include an introducer tube 340 and an elongate guide wire 335 inserted there through that each aid in the introduction of the delivery component 315 into the eye. As shown in FIG. 7A, the introducer tube 340 can be a generally longitudinally-extending shaft having a channel 345 running therethrough. The introducer tube 340 can have a sharpened tip 355 near a distal exit port 350 of the channel 345 (see FIGS. 9A-9B). The sharpened distal tip 355 of the introducer tube 340 can pass through the cornea 5 such that the introducer tube 340, guide wire 335 and device 105 of the delivery component 315 can be inserted into the anterior chamber 35 of the eye. The sharpened distal tip 355 of the introducer tube 340 can also be used to penetrate the trabecular meshwork 40 or other tissues near the trabecular meshwork 40, for example to access Schlemm's canal 45 or penetrate the iris root portion of the ciliary body. In an embodiment, the introducer tube 340 can be curved to achieve tangential entry into Schlemm's canal 45. In some implementations, the introducer tube 340 can be curved such as by forming an arc of a circle having a radius of curvature less than about 12 inches. In some implementations, the introducer tube 340 has a radius of curvature that is between about 10 and 12 inches. In some implementations, the introducer tube 340 has a radius of curvature that is between about 7 and 12 inches. In some implementations, the introducer tube 340 has a radius of curvature that is between about 5 and 12. In some implementations, the introducer tube 340 has a radius of curvature that is between about 5.5 and 7 inches. It should be appreciated that the introducer tube 340 can have other shapes and other curvatures.

As mentioned above, the introducer tube 340 in combination with the guide wire 335 can aid in the retention of the device 105 in its delivery configuration. The introducer tube 340 in combination with the guide wire 335 can also aid in the expansion and contraction of the device and/or the release of the device 105 into its deployed configuration at the target location in the eye (see FIGS. 7A-7C). The guide wire 335 can extend longitudinally through the channel 345 of the introducer tube 340 as well as through the internal passageway 120 of the device 105. The surface of the internal passageway 120 can be sufficiently smooth relative to the delivery device 305 to permit the device 105 to slide off of the delivery device 305 during the delivery process. The introducer tube 340 can be positioned axially over at least a portion of the device 105 such as the proximal end 110 of the device 105.

The distal tip 130 of the device 105 can have a shape that is symmetrical relative to a central, longitudinal axis of the device 105, such as a hemispheric tip, blunt-tipped cone, rounded-off cone tip. The blunt or atraumatic tip shape can aid in the gentle dissection through the eye tissues. Dynamics of the device 105 on the end of the guide wire 335 can be such that the device 105 and guide wire 335 do not inadvertently penetrate tissues, for example the walls of Schlemm's canal 45. The shape, structure, materials and material properties of the guide wire 335 are selected to optimize for insertion through the target eye tissues.

As best shown in FIG. 6B-6C, the actuator 320 can be used to control the guide wire 335 and/or the introducer tube 340. In a first state shown in FIG. 6B, the device 105 can be positioned within a distal end region of the introducer tube 340 and the guide wire 335 can be extended distally relative to the introducer tube 340 such that it abuts the distal, solid tip 130 of the device 105. The guide wire 335 can abut and press against the inside of the solid distal tip 130 and in combination with the introducer tube 340 maintain the device 105 in the delivery configuration. This arrangement between the device 105, the guide wire 335 and the introducer tube 340 can tension or stretch the device 105 into its delivery configuration characterized by a reduced diameter that is optimized for delivery through the anterior chamber 35. Movement of the actuator 320 can cause the introducer tube 340 to retract such that the device 105 is no longer retained by the introducer tube 340 and can expand to its deployed configuration. Similarly, sliding the guide wire 335 proximally into the introducer tube 340 as shown in FIG. 6C can release the tension on the device 105 and allow it to transition into its deployed configuration. The delivery device 305 can also incorporate a pusher that pushes the device 105 out from the channel 345 of the introducer tube 340 during implantation. In another embodiment, the expandable element is not released in the eye as will be described in more detail below. In this embodiment, the distal end 130 of the element 105 is coupled to the guide wire 335 and a proximal end 110 of the element 105 can be coupled to a sheath 340. The guide wire 335 can be urged proximally and/or the sheath 340 can be urged distally such that one or more portions of the element 105 expands radially outward.

The guide wire 335 (and/or the introducer tube 340) can have a cross-sectional size and shape that complements the cross-sectional shape of the inner passageway 120 of the device 105. The shape of the guide wire 335 along its long axis can be straight or it can be can be curved along all or a portion of its length in order to facilitate proper placement (see FIGS. 9A-9B). In the case of the curved guide wire 335, the radius of curvature can vary. For example, the guide wire 335 can have a radius of curvature of 3 mm to 50 mm and the curve can cover from 0 degrees to 180 degrees. In some embodiments, the guide wire 335 has a radius of curvature that corresponds to or complements the radius of curvature of a region of the eye, such as Schlemm's canal 45. In some embodiments, the radius of curvature can be approximately 11-12 mm. In some embodiments, the radius of curvature of the guide wire can be between 5-7 mm. Moreover, the radius of curvature can vary moving along the length of the guide wire 335. There can also be mechanism to vary the radius of curvature of portions of the guide wire 335 during placement.

As mentioned above, the device 105 can expand automatically such as upon withdrawal of the guidewire 335 and/or the introducer tube 340. For example, the device 105 can be self-expanding or incorporate a shape-memory material. In some embodiments, the device 105 can be actively expanded. In some embodiments, the device 105 can be loaded onto a balloon-tip catheter such that expansion of a balloon presses against the inner surface of the device 105 to cause its expansion into the deployed configuration.

It should also be appreciated that the devices described herein need not be released upon deployment to dilate tissues within the eye. For example, a device can be inserted to a target region of the eye in an unexpanded configuration, expanded and then returned to the unexpanded configuration and removed from the eye along with the delivery device. In some embodiments, the device can be inserted into Schlemm's canal in a reduced diameter configuration, expanded to impart a circumferential pressure along at least a portion of the canal creating a controlled trauma of the tissues by forming small tears resulting in an expanded canal. Once the tissues are expanded, the outer diameter of the device can be reduced such that the entire device can be removed from the eye leaving the tissues in a generally expanded state.

Figures 8A, 8B:
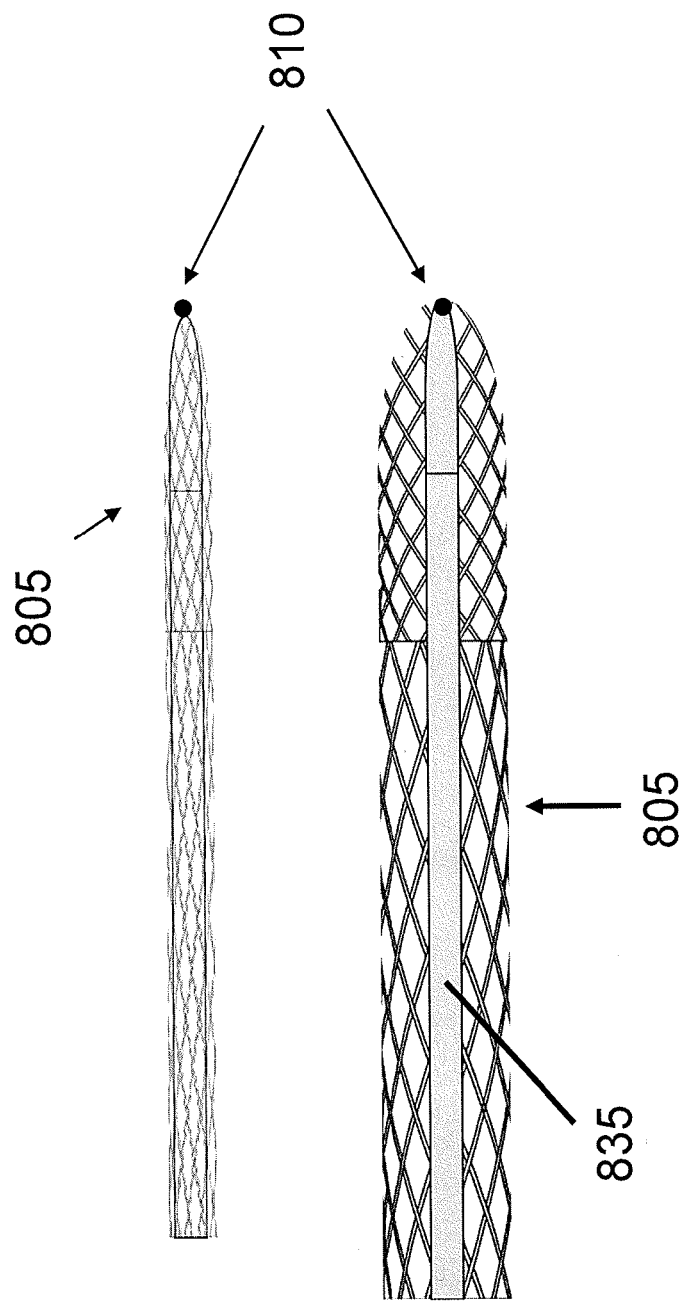
FIGS. 8A-8B show schematic views of an expandable element coupled to a distal portion of a guide wire.

FIGS. 8A-8B illustrate an embodiment of an expandable element 805 coupled to a distal region of a delivery device in an insertion configuration and an expanded configuration. The expandable element 805 can be a braided element having a gathered portion at a distal end coupled to the guide wire 835 at location 810, such as by a weld or other coupling mechanism. The expandable element 805 can encircle the guide wire 835 and be maintained in a reduced diameter configuration over the guide wire 835, for example, by advancing the guide wire 835 in a distal direction while restraining the proximal region of the expandable element 805 with an outer sheath (not shown) or other mechanism coupled to a proximal region of the expandable element 805. The delivery device is described in more detail above.

The braided expandable element 805 can expand the tissues, but still allow for fluid flow through the expandable element 805 while in the expanded state. It should be appreciated, however, that the expandable element 805 need not be braided. For example, the expandable element 805 can also be a fluid-tight expandable element such as a balloon or other closed element that can expand.

Once positioned within the eye, the expandable element 805 can be expanded such that it imparts a force against the surrounding tissues of the eye, and then contracted such that it can be removed from the eye. The expandable element 805 can expand radially about the entire circumference of the central shaft of the guide wire 835. The expandable element 805 can also expand along a portion of or in a particular orientation with respect to the central shaft of the guide wire 835. The shape of the expandable element 805 can include, but is not limited to, cylindrical, spherical, toroid, doughnut-like, conical, branched, pronged and other geometries. The expandable element 805 can expand such that the cross-sectional shape of the expandable element 805 is a semi-circular, oval, triangular shape, rectangular, single-humped, double-humped or other geometric shape. Further, the expandable element 805 can expand radially along the entire length or a smaller portion of the length. The length of the expandable element 805 can vary. In some embodiments, the length of the expandable element 805 is generally shorter than the circumferential length of Schlemm's canal.

Figure 10A:
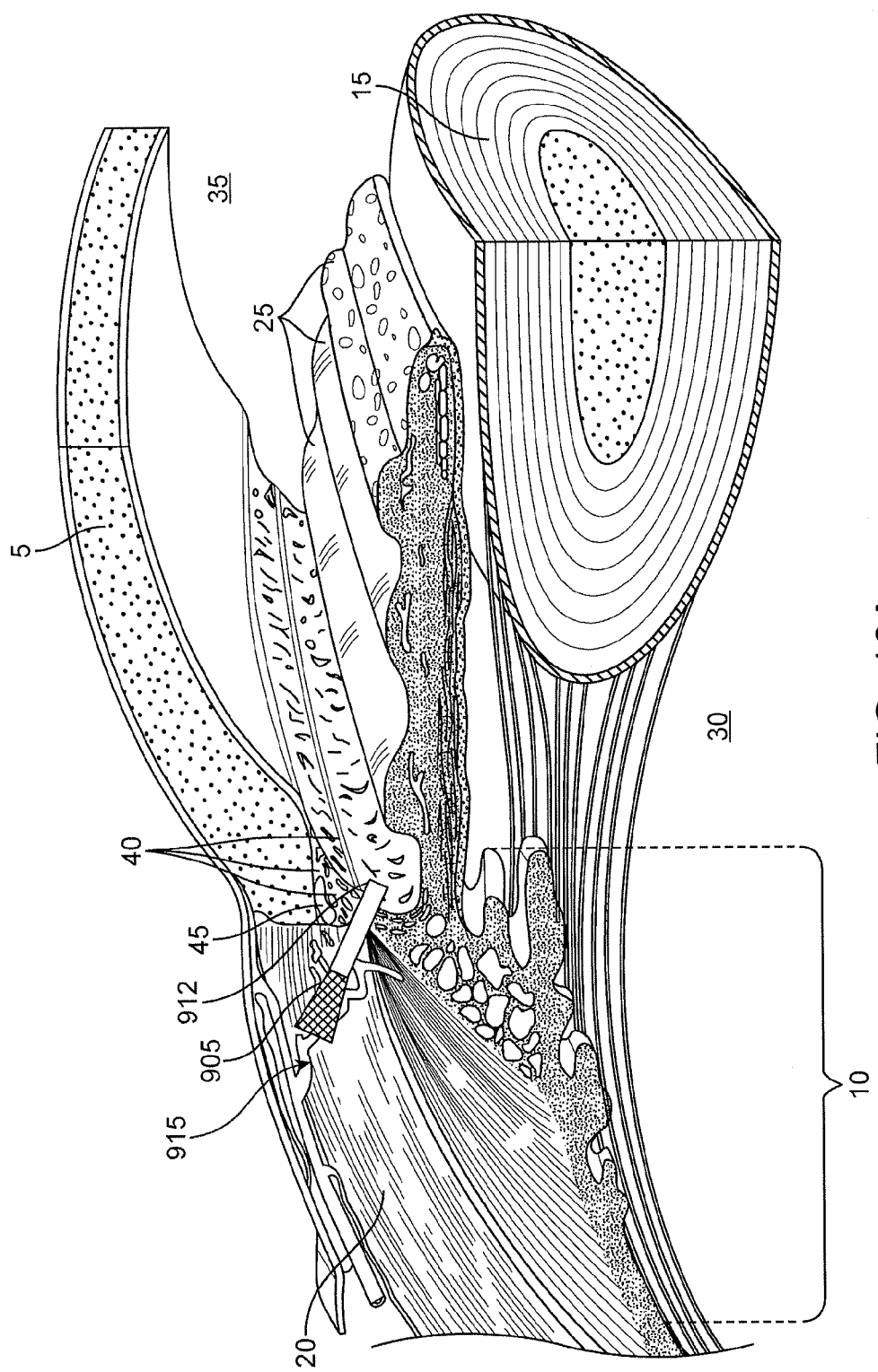
FIGS. 10A-10B show schematic views of an expanded device positioned near venous region of the sclera.
Figure 10B:
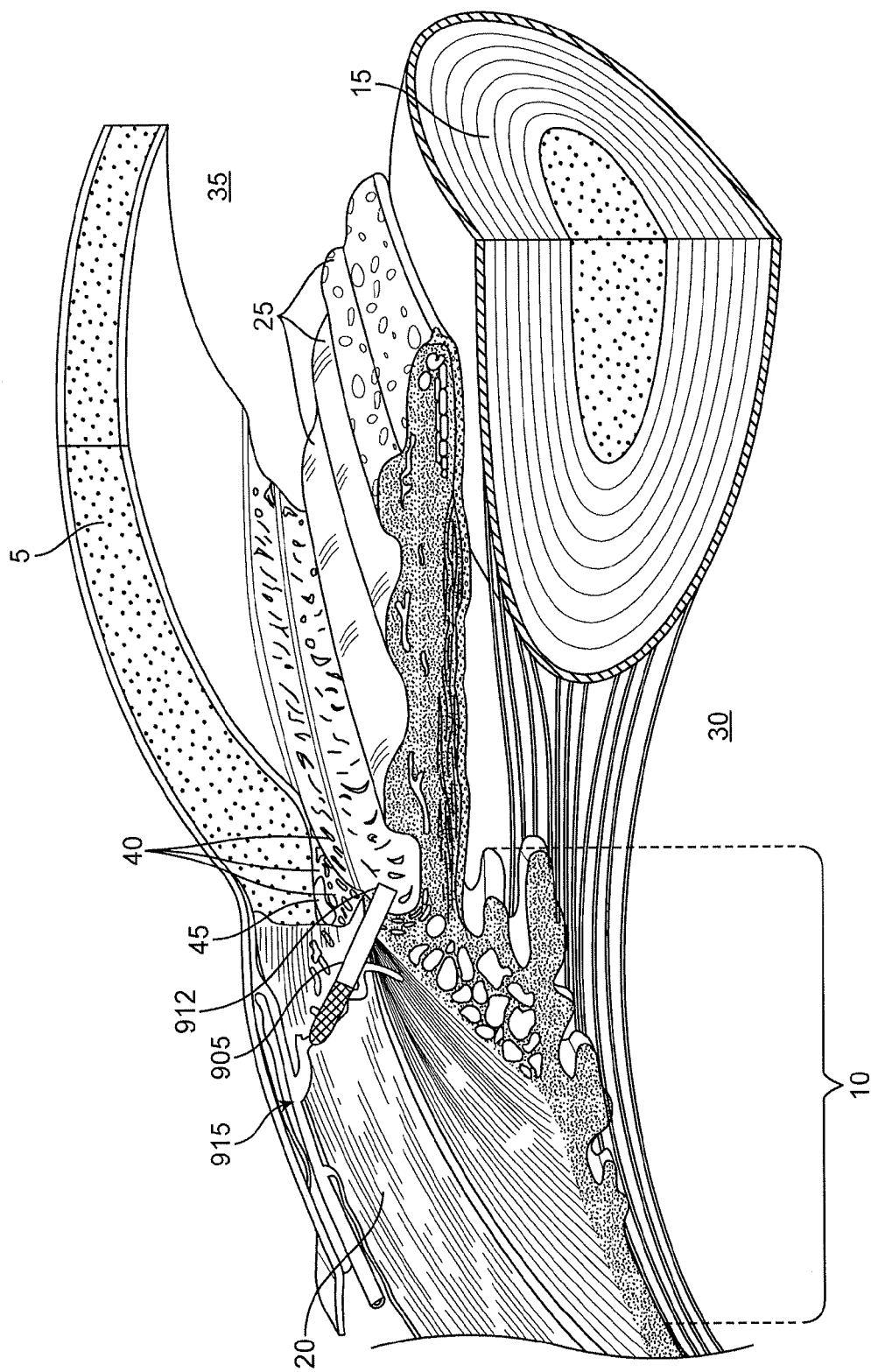

In some embodiments, the devices described herein can be inserted ab interno and directed towards the outside of the eye (see FIGS. 10A-10B). A delivery device with a device 905 coupled to the distal end can be used to tunnel through an inner portion of sclera 20 under the conjunctiva from within the anterior chamber 35. It should be appreciated that the device 905 can be releasably deployed such that it remains within the eye upon removal of the delivery device. It should be appreciated that the device 905 also can be expanded, unexpanded and removed such that it does not remain in the eye. In some embodiments, the device 905 does not penetrate all the way through the sclera 20, but remains within deep layers of the sclera 20 near where the veins 915 are located. The device 905 can be released such that a tunnel is stretched out and formed within the sclera 20 holding open a region near the venous outflow 915 portion of the sclera 20. Tissue separation can be sufficient to insert the device 905 from the anterior chamber 35 into the sclera 20 such that creating holes or excavated portions of the sclera 20 are avoided. An inlet 912 of the device 905 can remain open to the anterior chamber 35 such that aqueous humor can flow through the device 905 towards the venous outflow 915.

Methods of Use

A method of delivering a device into the eye is now described. It should be appreciated that the method of delivering a device should not be limited to devices that are expanded and released such that they remain within the eye. The device can also include an expandable element coupled to the distal end of the delivery device that can be expanded one or more times during insertion, but that is removed from the eye when the delivery device is removed. It should also be appreciated that although the method is described generally in terms of implantation within Schlemm's canal that the ab interno method can be performed in other regions within the eye, for example within the scleral tissues as shown in FIGS. 10A-10B or to create the supraciliary and/or suprachoroidal spaces.

As shown in FIGS. 9A-9B, the device 105 can be mounted onto a guide wire 335 of a delivery device 305 by inserting the guide wire 335 through the internal passageway 120 of the device 105. The introducer tube 340 can extend over at least the proximal end of the device 105 such that a friction fit is obtained between the outer surface of the device 105 and the channel 345 of the introducer tube 340. The guide wire 335 can be slightly extended in a distal direction using the actuator such that the guide wire 335 abuts the solid tip (not shown) of the device 105 to provide tension to the device 105 and maintain it in its narrow diameter delivery configuration. Alternatively, the entire device 105 can be contained within the channel 345 of the introducer tube 340 to maintain the device in the delivery configuration.

Implantation can be performed using a viewing lens (such as a gonioscopy lens positioned adjacent the cornea. The viewing lens enables viewing of internal regions of the eye, such as the angle of the eye, from a location in front of the eye. The viewing lens can optionally include one or more guide channels that are sized to receive the delivery portion 315 of the delivery system 305. The locations and orientations of the guide channels can vary depending on the angle and location where the device 105 is to be delivered. An operator can use the viewing lens during delivery of the device into the eye. The viewing lens can have a shape or cutout that permits the surgeon to use the viewing lens in a manner that does not cover or impede access to the corneal incision. Further, the viewing lens can act as a guide through which a delivery system 305 can be placed to predetermine the path of the device as it is inserted through the cornea.

An endoscope can also be used during delivery to aid in visualization. For example, a twenty-one to twenty-five gauge endoscope can be coupled to the device during delivery such as by mounting the endoscope along the side of the device or by mounting the endoscope coaxially within the device. Ultrasonic guidance can be used as well using high resolution bio-microscopy, OCT and the like. Alternatively, a small endoscope can be inserted though another limbal incision in the eye to image the tissue during the procedure. Each step of implantation can also be visualized using an internal visualization system (see for example U.S. Patent Application Publication No. 2010/0134759, filed Jun. 25, 2009, which is incorporated by reference in its entirety). Visualization can occur continuously during implantation or other procedures without the need for re-positioning or removing one or more components of the imaging systems and without the need for viewing through a goniolens. A fiber-optic beacon tip can be provided such that a direct visual location of the device can be performed. Optional external image guidance such as ultrasound imaging or optical coherence tomography can also be used. Accurate positioning within the target tissue can also be aided by features of the instrument such as markings to indicate length within the target tissue, coatings or markers to aid imaging, and markings to indicate rotational alignment. The instrument or device can also incorporate markers to assist in determining its location such as fluorescent or ultrasonically reflective coatings or radiopaque markers.

Again with respect to FIGS. 7A-7C, the delivery portion 315 of the delivery device 305 can be positioned such that the guide wire 335 extends through the internal passageway 120 of the device 105. The distal tip of the guide wire 335 can abut the inner surface of the solid tip 130 of the device 105. The guide wire 335 and the device 105 can each be received within the channel 345 of the introducer tube 340. Alternatively, the introducer tube 340 can extend over just a proximal portion 110 of the device 105 and the device 105 mounted on the guide wire 335 can be used to perform the dissection through tissues. The sharpened distal tip 355 of the introducer tube 340 can penetrate through the cornea 5 forming a small, corneal incision to access the anterior chamber 35. In this regard, the single incision can be made in the eye, such as within the limbus of the cornea 5. In some embodiments, the incision is very close to the limbus, such as either at the level of the limbus or within 2 mm of the limbus in the clear cornea 5. The introducer tube 340 can be used to make the incision or a separate cutting device can be used. For example, a knife-tipped device or diamond knife can be used to initially enter the cornea. A second device with a spatula tip can then be advanced over the knife tip wherein the plane of the spatula is positioned to coincide with the dissection plane.

The corneal incision can have a size that is sufficient to permit passage of the introducer tube 340 containing the device 105 on the guide wire 335. In some embodiments, the incision is about 1 mm in size. In some embodiments, the incision is no greater than about 2.85 mm in size. In some embodiments, the incision is no greater than about 2.85 mm and is greater than about 1.5 mm. It has been observed that an incision of up to 2.85 mm is a self-sealing incision. For clarity of illustration, the figures are not to scale.

After insertion through the corneal incision, the introducer tube 340 can be advanced into the anterior chamber 35 along a pathway that enables the device 105 to be delivered from the anterior chamber 35 to the angle of the eye. The device 105 can approach the angle of the eye from the same side of the anterior chamber 35 as the deployment location such that the device 105 does not have to be advanced across the iris 25. Alternately, the device 105 can approach the angle of the eye from across the anterior chamber 35 such that the device 105 is advanced across the iris 25 and/or the anterior chamber 35 toward the opposite angle of the eye. The device 105 can approach the angle of the eye along a variety of pathways. The device 105 does not necessarily cross over the eye and does not generally intersect the center axis of the eye. In other words, the corneal incision and the location where the device 105 can be implanted at the angle of the eye can be in the same quadrant when viewed looking toward the eye along the optical axis. Also, the pathway of the device from the corneal incision to the angle of the eye ought not to pass through the centerline of the eye to avoid interfering with the pupil.

The introducer tube 340 can be positioned for approach such that it can be advanced further into the eye and the sharpened distal tip 355 of the introducer tube 340 can penetrate tissue of the trabecular meshwork 40 or juxtacanalicular trabecular meshwork 50 near the angle of the eye and the inner wall of Schlemm's canal 45 adjacent to the anterior chamber 35. Anatomical landmarks such as the scleral spur and Schwalbe's line can be used as an indicator of where to advance the device 105 into the eye tissue.

The introducer tube 340 can cut through the trabecular meshwork 40 to place the distal exit port 350 of the introducer tube 340 into communication with Schlemm's canal 45. Alternatively, another method of creating the hole through the trabecular meshwork 40 can be performed. For example, an incision can be made with a microknife, irrigating knife, sharpened guide wire, applier or another applicator. A retinal pick or microcurrette can also be used as can retrograde fiberoptic laser ablation.

Figure 7B:
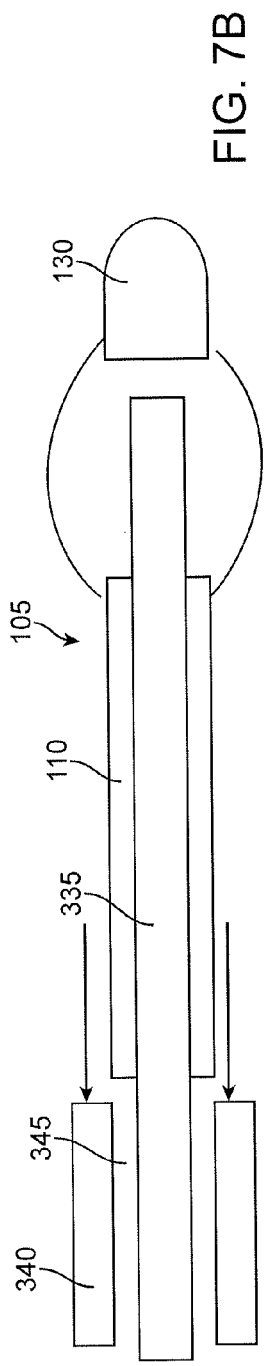
Figure 7C:
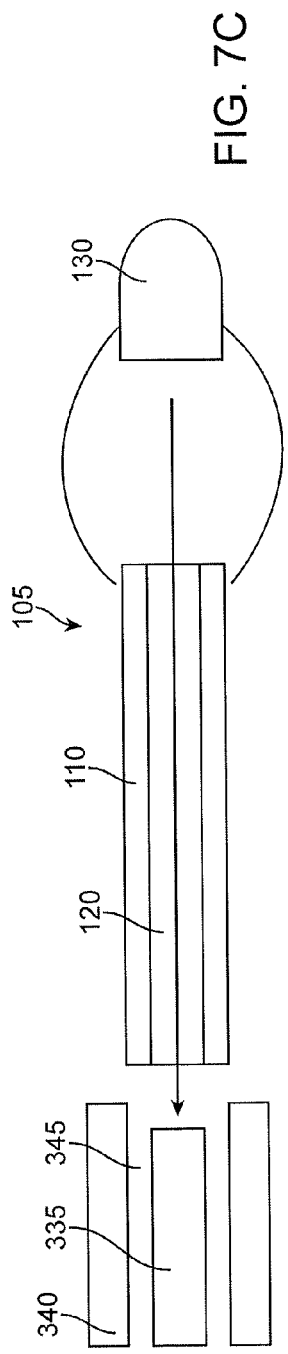

Once the device 105 has been advanced or threaded a sufficient distance into Schlemm's canal 45, the introducer tube 340 can be withdrawn in a proximal direction by actuating the actuator 320 such that the guide wire 335 and device 105 mounted thereon extend out the distal exit port 350 of the introducer tube 340 as shown in FIG. 7B. Once the introducer tube 340 is no longer in contact with the device 105, the device 105 is no longer under tension and can undergo transition into its expanded, deployed configuration (see FIG. 7B). Alternatively, the device 105 need not be self-expanding and can use an active expansion device such as a balloon tip catheter to expand its diameter into the deployed configuration. The guide wire 335 can be withdrawn to completely disengage the device 105 from the delivery system 305 (see FIG. 7C). The delivery system 305 can then be removed from the eye and the expanded device 105 remains within the Schlemm's canal 45. It should be appreciated that the device need not remain within the eye tissues or be releasably deployed from the delivery device. The device can be reversibly expanded and removed from the eye as described in detail above.

The device 105 in its expanded, deployed configuration can extend through the trabecular meshwork 40 and/or juxtacanalicular trabecular meshwork 50 to maintain a pathway between the anterior chamber 35 and Schlemm's canal 45. The device 105 can also serve as a support scaffolding to maintain the patency of Schlemm's canal 45 to facilitate the outflow of fluid from the anterior chamber 35 into Schlemm's canal 45 and subsequently into the aqueous collector channels and the aqueous veins to reduce intraocular pressure. Alternatively, one or more portions of the device 105 can be somewhat larger than the inner size of Schlemm's canal 45 such that when the device 105 is expanded into the deployed configuration the device 105 can apply a tension force to the tissue and increase its permeability for fluid flow.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A system for treating an ocular disorder in an eye, comprising:
   an ocular device comprising:
   a proximal end, a distal end, and an internal lumen forming a flow pathway extending from the proximal end to the distal end wherein upon implantation in the eye the proximal end is configured to be in fluid communication with Schlemm's canal of the eye and the distal end is configured to be in fluid communication with an anterior chamber of the eye;
   at least one inflow region communicating with the flow pathway; and
   an expandable portion comprising a plurality of interconnected struts forming multiple openings in the device that communicate with the flow pathway, wherein the expandable portion has a first diameter of a generally cylindrical first cross-sectional shape suitable for insertion into the eye through a self-sealing incision in the cornea and a second diameter of a second cross-sectional shape that is larger than the first diameter and sized to expand the general circumference of the surrounding tissue, the second cross-sectional shape being generally oval and configured to conform to the contour of the Schlemm's canal and prevent rotation of the ocular device upon expansion; and
   a delivery device for inserting the ocular device into an eye, the delivery device comprising:

a sheath configured to surround at least a portion of the ocular device;

an applier configured to insert into the internal lumen of the ocular device; and an actuator.

2. The system of claim 1, wherein the expandable portion of the ocular device is located near the distal end and the second cross-sectional shape of the ocular device is funnel-shaped.

3. The system of claim 1, wherein the interconnected struts of the ocular device are braided or woven.

4. The system of claim 1, wherein the ocular device comprises a tube having cut-outs forming the interconnected struts.

5. The system of claim 1, wherein the second diameter of the ocular device is between about 75% and about 100% larger than the first diameter.

6. The system of claim 1, wherein at least a portion of the ocular device is coated with a flexible material.

7. The system of claim 1, wherein the expandable portion of the ocular device is self-expanding.

8. The system of claim 1, wherein the expandable portion of the ocular device is configured to be actively expanded.

9. The system of claim 8, wherein the expandable portion is configured to be actively expanded with a balloon coupled to the applier.

10. The system of claim 1, wherein the ocular device is positioned in the eye such that the inflow region communicates with the anterior chamber.

11. The system of claim 10, wherein one or more of the openings communicate with at least one tissue structure near an anterior angle of the eye, wherein the tissue structure is selected from the group consisting of trabecular meshwork, juxtacanalicular structure, aqueous vein, episcleral vein, Schlemm's canal, a collecting channel, sclera, supraciliary space and suprachoroidal space.

12. The system of claim 11, wherein the ocular device is configured to conform to a contour of the tissue structure surrounding the ocular device.

13. The system of claim 1, wherein the ocular device is advanced around Schlemm's canal up to about 340 degrees.

14. The system of claim 1, wherein the ocular device has a length that extends from the anterior chamber to a portion of Schlemm's canal.

15. The system of claim 1, wherein the distal end of the ocular device is closed.

16. The system of claim 15, wherein the distal end of the ocular device is permanently coupled to the applier and the ocular device is not releaseably deployed within the eye.

17. The system of claim 16, wherein following expansion to the second diameter the expandable portion is returned to the first diameter and removed from the eye.

18. A method for the surgical treatment of an ocular disorder in an eye, comprising:

coupling an ocular stent device to a delivery device comprising an applier, a sheath, and an actuator;

forming a self-sealing incision in the cornea;

introducing the ocular stent device into the anterior chamber of the eye through the incision using the delivery device, the ocular stent device comprising:

a proximal end, a distal end, and an internal lumen forming a flow pathway extending from the proximal end to the distal end wherein upon implantation in the eye the proximal end is configured to be in fluid communication with Schlemm's canal of the eye and the distal end is configured to be in fluid communication with an anterior chamber of the eye;

an inflow region near the proximal end communicating with the flow pathway; and an expandable region comprising a plurality of interconnected struts forming multiple openings communicating with the flow pathway, wherein the expandable region has a first diameter of a generally cylindrical first cross-sectional shape suitable for insertion into the eye through the self-sealing incision in the cornea and a second diameter of a second cross-sectional shape that is larger than the first diameter and sized to expand the general circumference of the surrounding tissue, the second cross-sectional shape being generally oval and configured to conform to the contour of the Schlemm's canal and prevent rotation of the ocular device upon expansion;

inserting the distal end of the ocular stent device into a tissue structure near an anterior angle of the eye such that the inflow region remains in communication with the anterior chamber and at least a portion of the expandable region is positioned within the tissue structure;

expanding the expandable region; and conducting aqueous humor from the anterior chamber towards the tissue structure.

19. The method of claim 18, wherein expanding the expandable region comprises uncoupling the delivery device from the ocular stent device allowing the expandable region to passively expand.

20. The method of claim 18, wherein expanding the expandable region comprises actively expanding the expandable region with the delivery device.

21. The method of claim 18, wherein the second cross-sectional shape comprises a funnel shape.

22. The method of claim 18, wherein inserting the distal end of the ocular stent device into the tissue structure comprises inserting the distal end of the ocular stent device into at least one of a trabecular meshwork, juxtacanalicular structure, collecting channel, aqueous vein, episcleral vein, Schlemm's canal, sclera, supraciliary space and suprachoroidal space.

23. The method of claim 22, further comprising returning the expandable region to the first cross-sectional shape.

24. The method of claim 23, further comprising removing the ocular stent device from the eye.

25. The method of claim 24, wherein the tissue structure is maintained in an expanded configuration after removal of the ocular stent device from the eye.

26. The method of claim 18, wherein inserting the distal end of the ocular stent device into the tissue structure comprises creating an opening in the tissue structure.

* * * * *